(12) United States Patent
Eidenschink et al.

(10) Patent No.: US 11,992,645 B2
(45) Date of Patent: May 28, 2024

(54) INTEGRATED HEMOSTASIS BYPASS VALVE

(71) Applicant: St. Jude Medical, Cardiology Division, Inc., St. Paul, MN (US)

(72) Inventors: Tracee Eidenschink, Wayzata, MN (US); Mathias C. Glimsdale, St. Michael, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 253 days.

(21) Appl. No.: 17/668,542

(22) Filed: Feb. 10, 2022

(65) Prior Publication Data

US 2023/0248956 A1  Aug. 10, 2023

(51) Int. Cl.
*A61M 39/06* (2006.01)
*A61B 17/00* (2006.01)
(Continued)

(52) U.S. Cl.
CPC ......... *A61M 39/06* (2013.01); *A61B 17/0057* (2013.01); *A61B 2017/00623* (2013.01); *A61B 2017/00632* (2013.01); *A61B 2017/00867* (2013.01); *A61B 2017/3425* (2013.01); *A61M 2039/0258* (2013.01); *A61M 2039/0279* (2013.01); *A61M 2039/0282* (2013.01); *A61M 2039/0626* (2013.01)

(58) Field of Classification Search
CPC .......... A61M 39/06; A61M 2039/0626; A61M 2039/0258
See application file for complete search history.

(56) References Cited

U.S. PATENT DOCUMENTS 5,222,974 A 6/1993 Kensey
5,458,640 A * 10/1995 Gerrone ............. A61B 17/3462
604/249

(Continued)

FOREIGN PATENT DOCUMENTS

| EP | 1250171 B1 | 9/2004 |
|---|---|---|
| EP | 2018196 B1 | 4/2012 |
| WO | 9934849 | 7/1999 |

OTHER PUBLICATIONS

10th Global Left Atrial Appendage Occlusion Summit 2021, "LAAO Summit Program" (Mar. 26, 2021) 2 pgs.

(Continued)

*Primary Examiner* — Alexander J Orkin
(74) *Attorney, Agent, or Firm* — SLEMAN & LUND LLP

(57) ABSTRACT

According to one aspect of the disclosure, a delivery device may include a handle, a catheter sheath extending distally from the handle, and a hemostasis valve positioned within the handle. The hemostasis valve may be located proximal the catheter sheath and distal to a proximal end of the handle. The delivery device may also include a hemostasis bypass assembly coupled to the handle. The hemostasis bypass assembly may include a bypass tube coupled to an actuator. The actuator may be configured to be transitioned between a first condition in which a distal end of the bypass tube is positioned proximal to the hemostasis valve and the hemostasis valve is closed, and a second condition in which the distal end of the bypass tube traverses the hemostasis valve and the hemostasis valve is opened.

18 Claims, 11 Drawing Sheets

(51) Int. Cl.
  *A61B 17/34* (2006.01)
  *A61M 39/02* (2006.01)

(56) References Cited

U.S. PATENT DOCUMENTS

| | | | |
|---|---|---|---|
| 5,911,710 A * | 6/1999 | Barry | A61M 39/0693 604/167.04 |
| 6,276,661 B1 | 8/2001 | Laird | |
| 6,331,176 B1 | 12/2001 | Becker | |
| 6,551,283 B1 | 4/2003 | Guo et al. | |
| 6,632,200 B2 | 10/2003 | Guo et al. | |
| 7,081,106 B1 | 7/2006 | Guo et al. | |
| 7,335,182 B1 * | 2/2008 | Hilaire | A61M 39/06 604/27 |
| 7,691,095 B2 | 4/2010 | Bednarek et al. | |
| 7,823,258 B2 | 11/2010 | Tegg | |
| 7,914,515 B2 | 3/2011 | Heideman et al. | |
| 8,043,263 B2 | 10/2011 | Helgeson | |
| 8,231,569 B2 | 7/2012 | Grasse et al. | |
| 8,323,239 B2 | 12/2012 | Bednarek et al. | |
| 8,357,119 B2 | 1/2013 | Stout | |
| 8,361,020 B2 | 1/2013 | Stout | |
| 8,388,583 B2 | 3/2013 | Stout | |
| 8,469,928 B2 | 6/2013 | Stout | |
| 8,480,636 B2 | 7/2013 | Khieu et al. | |
| 8,574,203 B2 | 11/2013 | Stout | |
| 8,603,066 B2 | 12/2013 | Heidman et al. | |
| 8,679,063 B2 | 3/2014 | Stout | |
| 9,101,746 B2 | 8/2015 | Stout | |
| 9,114,241 B2 | 8/2015 | Stout | |
| 9,132,258 B2 | 9/2015 | Bednarek et al. | |
| 9,173,642 B2 | 11/2015 | Blaskowski et al. | |
| 9,259,813 B2 | 2/2016 | Heideman et al. | |
| 9,320,503 B2 | 4/2016 | Bolduc | |
| 9,492,636 B2 | 11/2016 | Heideman et al. | |
| 10,035,000 B2 | 7/2018 | Bednarek et al. | |
| 10,130,791 B2 | 11/2018 | Heideman et al. | |
| 10,201,337 B2 | 2/2019 | Glimsdale | |
| 10,569,072 B2 | 2/2020 | Agrawal | |
| 10,737,086 B2 | 8/2020 | Agrawal | |
| 10,842,981 B2 | 11/2020 | Agrawal | |
| 10,953,214 B2 | 3/2021 | Bhatnagar | |
| 10,960,501 B2 | 3/2021 | Agrawal | |
| 11,291,821 B2 | 4/2022 | Agrawal | |
| 11,510,779 B2 | 11/2022 | Marchand | |
| 2001/0021825 A1 * | 9/2001 | Becker | A61M 39/06 604/167.04 |
| 2004/0044350 A1 * | 3/2004 | Martin | A61B 18/1492 606/139 |
| 2007/0066993 A1 * | 3/2007 | Kreidler | A61B 17/12122 606/213 |
| 2009/0270813 A1 | 10/2009 | Moreno, Jr. | |
| 2010/0280463 A1 * | 11/2010 | Murayama | B05D 5/08 251/366 |
| 2018/0126143 A1 | 5/2018 | Agrawal | |
| 2018/0256872 A1 * | 9/2018 | Agrawal | A61M 39/06 |
| 2019/0351210 A1 * | 11/2019 | Solomon | A61M 25/0075 |
| 2020/0390549 A1 | 12/2020 | Marchand | |
| 2021/0379337 A1 | 12/2021 | Yamamoto | |
| 2021/0393920 A1 * | 12/2021 | Yamamoto | A61M 25/0097 |
| 2023/0270992 A1 * | 8/2023 | Eidenschink | A61M 39/0613 604/167.01 |

OTHER PUBLICATIONS

10th Global Left Atrial Appendage Occlusion Summit 2021, "Screen Grabs from LAAO Submit Webinar" (Mar. 26, 2021) 4 pgs.
Abbott MediaRoom Press Release—Amulet Steerable Sheath, "Abbott Receives European and Canadian Approval for Amplatzer Steerable Delivery Sheath to Optimize Left Atrial Appendage Closure Procedures for People at Risk of Stroke" (Jun. 7, 2021) 2 pgs.

* cited by examiner

INTEGRATED HEMOSTASIS BYPASS VALVE

BACKGROUND

Catheters are frequently used to assist in the delivery of medical devices into a patient non-invasively. For example, several types of collapsible and expandable medical devices may be delivered to, and implanted within, the heart of a patient using a catheter that is advanced through the vasculature and into the patient's heart without needing to make any incisions in the patient's chest or heart, and without needing to put the patient on cardiopulmonary bypass.

Left atrial appendage ("LAA") occluder devices are one example of collapsible and expandable medical devices that may be delivered to a patient's heart via a catheter that traverses the patient's vasculature. In some examples, a catheter may be advanced through the patient's femoral vein, into the right atrium through the inferior vena cava, across the atrial septum and into the left atrium, with a distal end of the catheter positioned within or adjacent to the LAA. The LAA occluder device may be within the catheter during the advancement of the catheter, or otherwise may be advanced through the catheter after the catheter is already in the desired position. The LAA occluder may be in a collapsed state with a relatively small profile while inside the catheter, and may self-expand into the LAA upon deployment from the distal end of the catheter. One such LAA occluder is the Amplatzer™ Amulet™ Occluder offered by Abbott Labs. One example of a LAA occluder device is described in U.S. Pat. No. 10,201,337, the disclosure of which is hereby incorporated by reference herein.

As explained in greater detail below, although this disclosure generally focuses on a hemostasis bypass valve in the context of a steerable sheath for delivering a LAA occluder, the disclosure is not so limited, and may apply to various other types of sheaths (including non-steerable sheaths) and various other types of medical devices to be delivered (including other occluder-type devices, such as PFO closure devices, and other devices that are not occluders).

BRIEF SUMMARY

According to one aspect of the disclosure, a delivery device may include a handle, a catheter sheath extending distally from the handle, and a hemostasis valve positioned within the handle. The hemostasis valve may be located proximal the catheter sheath and distal to a proximal end of the handle. The delivery device may also include a hemostasis bypass assembly coupled to the handle. The hemostasis bypass assembly may include a bypass tube coupled to an actuator. The actuator may be configured to be transitioned between a first condition in which a distal end of the bypass tube is positioned proximal to the hemostasis valve and the hemostasis valve is closed, and a second condition in which the distal end of the bypass tube traverses the hemostasis valve and the hemostasis valve is opened.

According to another aspect of the disclosure, a medical device system includes the delivery device described in the above paragraph, and a collapsible and expandable medical device, the medical device configured to be received within the delivery device in a collapsed condition and configured to pass through the delivery device while in the collapsed condition, the medical device having a first column strength in the collapsed condition that is less than a column strength of the bypass tube.

DETAILED DESCRIPTION

As used herein, the term proximal refers to a position relatively close to a user of a medical device, while the term distal refers to a position relatively far from the user of the medical device, when the medical device is being used in an intended manner. In other words, the leading end of a medical device is positioned distal to the trailing end of the medical device.

Figure 1:
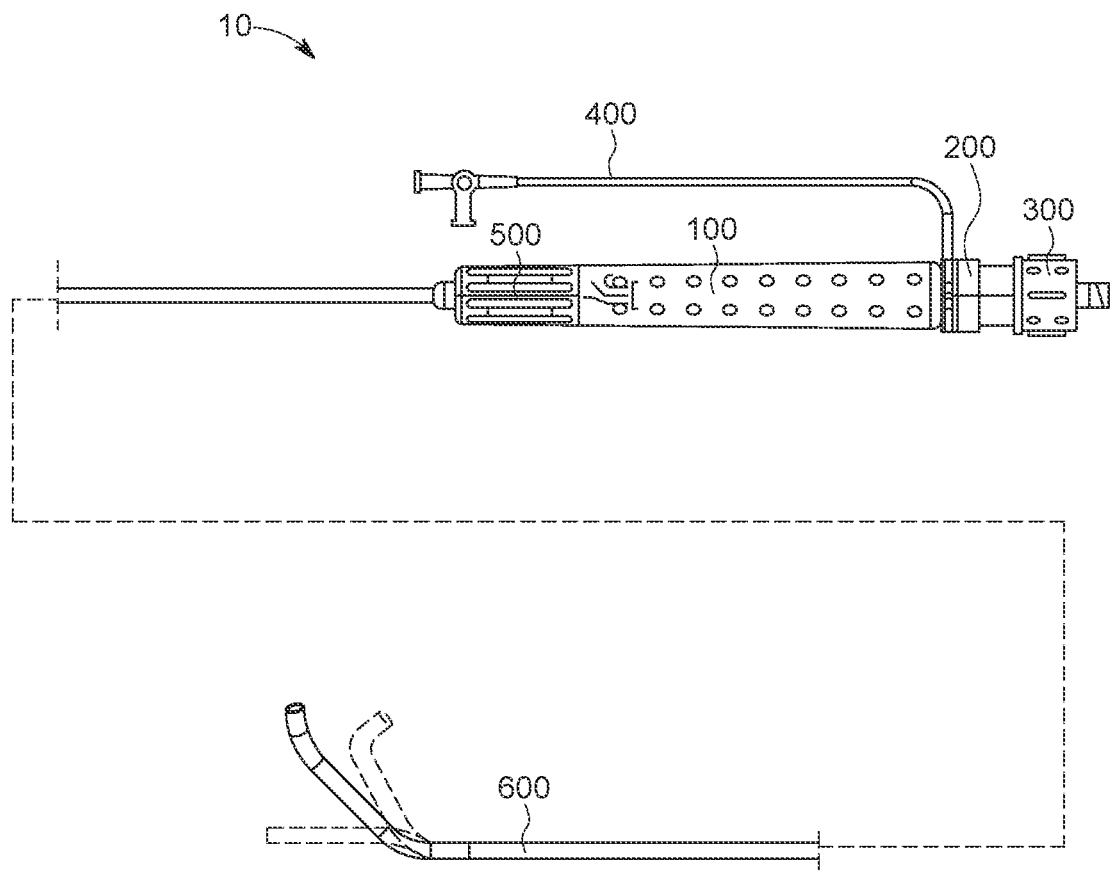
FIG. 1 is a schematic view of a steerable sheath according to one aspect of the disclosure.

FIG. 1 illustrates a delivery device 10, which in the illustrated embodiment is a steerable sheath, although it should be understood that the inventive concepts disclosed herein may be used in conjunction with other catheter or sheath devices, whether or not steerable. Generally, delivery device 10 includes a handle 100, a hemostasis valve assembly 200 at a proximal end of the handle 100, a hemostasis valve knob (or actuator) 300, a flushing tube 400, a deflection knob 500 at a distal end of the handle 100, and a deflectable sheath 600 extending from a distal end of the deflection knob 500 to a terminal distal end of the delivery device 10. This disclosure focuses on the hemostasis valve assembly 200 and the hemostasis valve knob 300, and the remainder of the delivery device 10 is generally described for the purpose of providing a contextual example of the use of the hemostasis valve assembly 200 and hemostasis valve knob 300. Thus, it should be understood that the hemostasis valve assembly 200 and hemostasis valve knob 300 described herein (including the optional variations described therewith) may be applicable to any suitable delivery device in which a hemostasis valve is desired. Delivery device 10 is particularly suited for delivery of a collapsible and expandable LAA occluder, but it should be understood that the delivery device 10 may be suited to delivery of other medical devices.

The handle 100 may be a generally cylindrical or otherwise shaped member that the user of the delivery device 10 may grip during use. The handle 100 may be at least partially hollow and house various components therein, and may have one or more internal lumens so that medical devices may be passed through the delivery device 10 from the proximal end to and beyond the terminal distal end of the delivery device 10. The handle 100 may be rotatably coupled to the deflection knob 500, with the deflection knob 500 being rotatable about the central longitudinal axis of the handle 100. The deflection knob 500 may be operably coupled to two pull wires that traverse the deflectable sheath 600 and which are fixed to anchors (or pull rings or similar structures) near the distal tip of the sheath 600. Rotation of the deflection knob 500 in a first rotational direction may deflect the distal tip of the sheath 600 in a first deflection direction, while rotation of the deflection knob 500 in a second opposite rotational direction may deflect the distal tip of the sheath 600 in a second deflection direction opposite the first deflection direction. In one exemplary embodiment, the distal tip of the sheath may have a neutral angled position of about 45 degrees relative to the central longitudinal axis of the delivery device 10, with a maximum deflection (upon rotation of the deflection knob 500 in the first, e.g. clockwise, rotational direction) of about 120 degrees (shown in phantom lines in FIG. 1) relative to the central longitudinal axis of the delivery device 10, and a minimum deflection (upon rotation of the deflection knob 500 in the second, e.g. counterclockwise, rotational direction) of about 0 degrees (shown in phantom lines in FIG. 1) relative to the central longitudinal axis of the delivery device 10. In one example, the proximal end of each pull wire may be coupled to an axially slideable component within handle 100, where rotation of the deflection knob 500 causes the two axially slideable components to slide axially in opposite directions. Suitable pull wire mechanisms are described in greater detail in U.S. Pat. No. 7,691,095, the disclosure of which is hereby incorporated by reference herein. The deflection mechanisms and ranges described above are merely exemplary, and as noted above, steering or deflection control may in some embodiments be entirely omitted from delivery device 10.

The catheter 600 may define a lumen therethrough configured to allow other devices to pass through the lumen. The catheter 600 may be formed from any suitable materials and in any suitable configuration. In one example, the catheter 600 includes an innermost liner layer, a torque transfer layer surrounding at least portions of the inner layer, and an outer sheath formed over the torque transfer layer. The wall of the catheter 600 may define lumens as well, for example two lumens spaced about 180 degrees apart, to accommodate the pull wires therethrough. Examples of suitable methods and materials for use in forming the catheter 600 are described in greater detail in U.S. Pat. No. 7,914,515, the disclosure of which is hereby incorporated by reference herein. However, it should be understood that the hemostasis valve assembly 200 and hemostasis valve knob 300 may be used with any suitable catheter configuration.

Flushing tube 400 may be a tube with a valve (e.g. luer lock) or connector at a proximal end thereof, with the distal end of the flushing tube 400 being in fluid communication with hemostasis valve assembly 200. The flushing tube 400 may be utilized to introduce fluid into and through the delivery device 10, for example to purge air out of the delivery device 10 prior to use. Flushing tubes are generally well known as they pertain to delivery devices, and thus flushing tube 400 is not described in greater detail herein.

Figure 2:
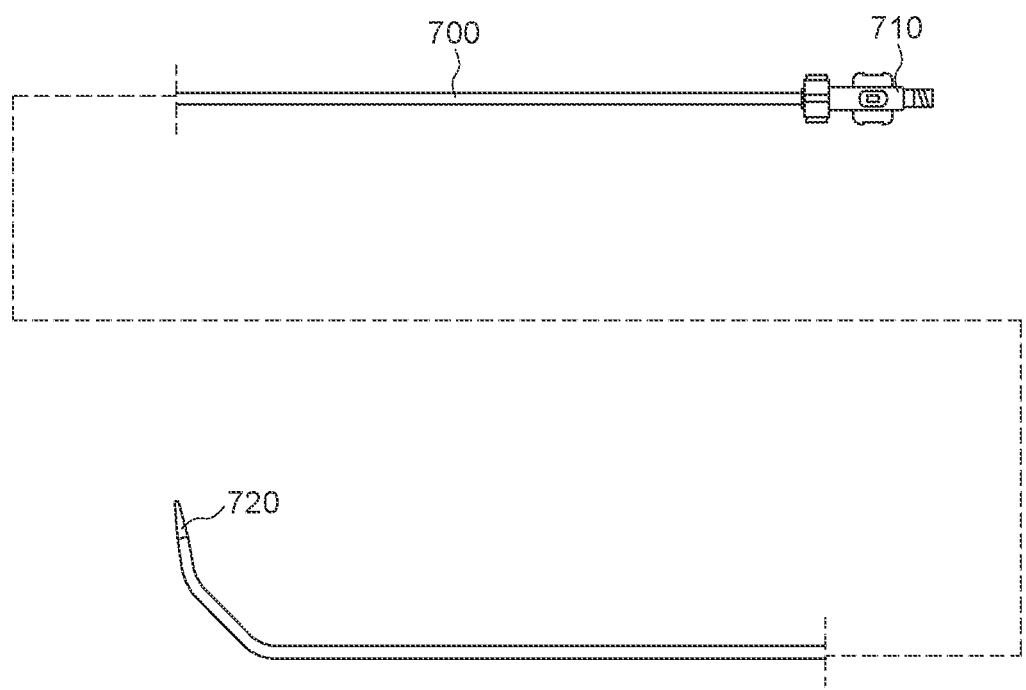
FIG. 2 is a schematic view of a dilator for use with the steerable sheath of FIG. 1.

FIG. 2 illustrates a dilator 700 that may be used with delivery device 10. In the illustrated example, dilator 700 is a solid member that includes a connector 710 such as a luer lock at a proximal end thereof, and an atraumatic tip 720 at a distal end thereof. Although referred to as a "solid member," it should be understood that dilator 700 may include a guidewire lumen passing therethrough to allow for the dilator 700 to ride over a guidewire. In other words, dilator 700 may also be thought of as a "substantially solid" or thick-walled device. The distal end portion of the dilator 700 may, in the absence of applied forces, have an angle of about 45 degrees relative to the central longitudinal axis of the dilator 700. In other words, the dilator 700 may include a distal portion that has a neutral angle that is about the same as the neutral angle of the distal tip of the catheter 600, whether that angle is about 45 degrees or another value. The dilator 700 may have an outer diameter that is about equal to (or slightly smaller than) the inner diameter of the catheter 600. As will be described in greater detail below, the dilator 700 may be positioned within and through the catheter 600 during delivery of the delivery device 10 to the desired anatomical location. Then the dilator 700 may be removed to allow for other devices, such as an LAA occluder, to be passed into and through the delivery device 10 for implantation.

Figure 3A:
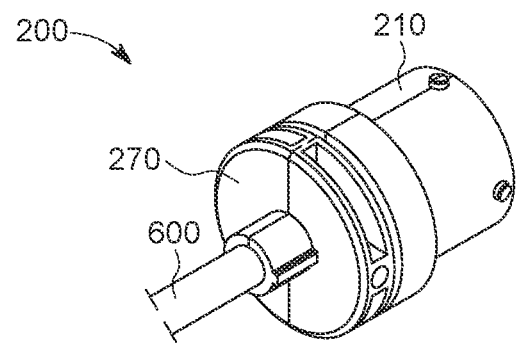
FIG. 3A is a perspective view of a hemostasis valve assembly of the steerable sheath of FIG. 1.
Figure 3B:
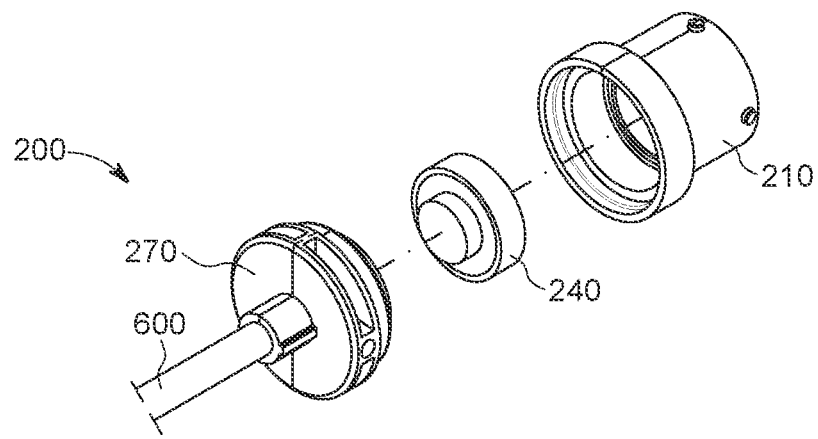
FIG. 3B is an exploded view of the hemostasis valve assembly of FIG. 3A.

FIG. 3A shows hemostasis valve assembly 200. In the assembled condition, a cap 210 of the hemostasis valve assembly is coupled to a hub 270 of the hemostasis valve assembly, and a proximal end of the catheter 600 is coupled to a distal end of the hub 270. Although not shown in FIG. 3A, the handle 100 may be coupled to and extend from a distal end of the hub 270. FIG. 3B shows hemostasis valve assembly 200 in an exploded view, showing that the hemostasis valve 240 provides a seal between the cap 210 and the hub 270 in the assembled condition of the hemostasis valve assembly 200.

Figure 3C:
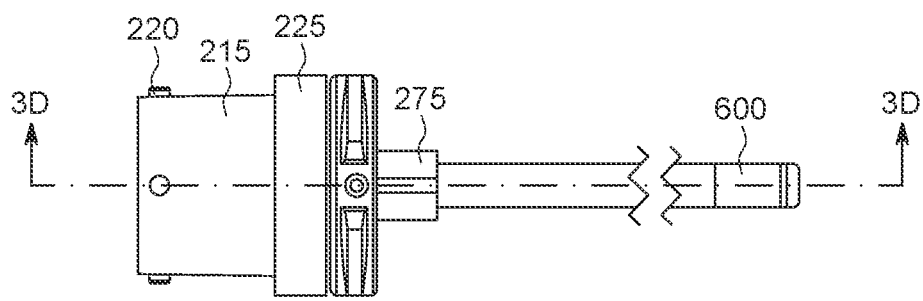
FIG. 3C is a side view of the hemostasis valve assembly of FIG. 3A.
Figure 3D:
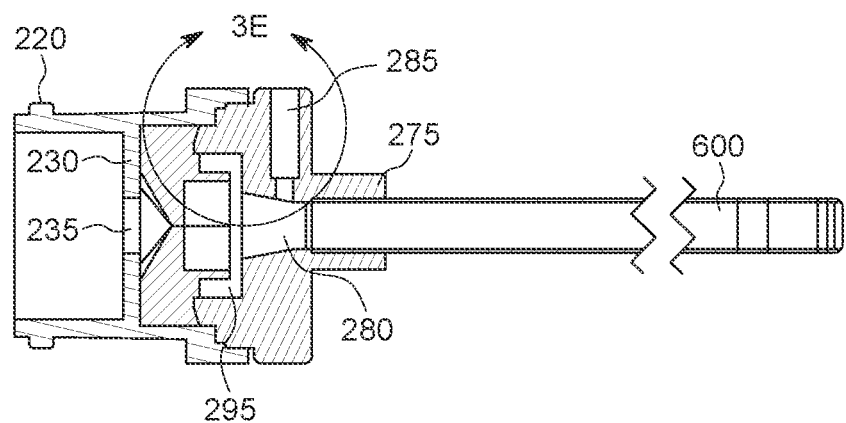
FIG. 3D is a cross-section of the hemostasis valve assembly of FIG. 3A taken along the section line 3D-3D of FIG. 3C.
Figure 3E:
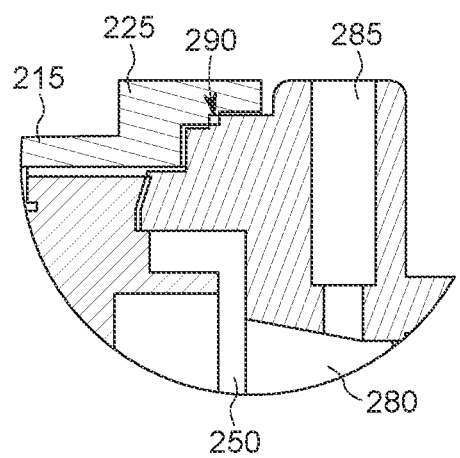
FIG. 3E is an enlarged isolated view of portion 3E of FIG. 3D.

Referring to FIGS. 3C-D, the proximal end of the catheter 600 may be received within and coupled to an extension 275 (e.g. a cylindrical extension) extending distally from a center of the hub 270. The interior of the cylindrical extension may be open such that, in the assembled condition, the inner lumen of catheter 600 is accessible from a proximal end of hub 270, via hemostasis valve 240, as described in greater detail below. The hub 270 may form a central aperture 280, which in the illustrated embodiment, is tapered from a relatively large proximal diameter, to a relatively small distal diameter where the central aperture 280 opens to the interior of the extension 275 and to the inner lumen of the catheter 600. The hub 270 may also define a flush port 285 that has a first end open to the exterior of the hub 270, and a second opposite end that opens to the central aperture 280. The flush port 285 is configured to couple to flushing tube 400, so that fluid pushed through the flushing tube 400 enters the hub 270 distal to the hemostasis valve 240, allowing for flushing and/or de-airing of the interior of the delivery device 10. Referring to FIGS. 3D-E, the hub 270 may also include reduced outer diameter portions 290, which may be provided as stepped down diameters that form shoulders, extending proximally. With this configuration, correspondingly sized and/or shaped distal portions of the cap 210 may be coupled to the hub 270 at those locations, for example via ultrasonic welding, with the resulting assembly having a generally smooth outer diameter between the transition from the cap 210 to the hub 270. Lastly, the hub 270 may define a generally cylindrical recess 295 at a proximal end thereof, for example radially inwardly of the stepped portions 290 and proximal to the central aperture 280. This recess 295 may be sized and shaped to receive a distal portion of the hemostasis valve 240 therein in the assembled condition of the hemostasis valve assembly 200.

Referring now to FIGS. 3A-D, cap 210 may include a main body 215 at its proximal end, which may be generally cylindrical and hollow. The main body 215 may include one or more protrusions 220 extending radially outward therefrom for interaction with the hemostasis valve knob 300, described in greater detail below. In the illustrated embodiment, each protrusion 220 is a cylindrical boss, and a total of four bosses are provided at about 90 degree spacing around the outer circumference of the main body 215. However, in other embodiments, more or fewer protrusions 220 may be provided, at the same or different relative spacing, and with shapes that are similar to or different than cylindrical bosses. At its distal end, the cap 210 may transition from main body 215 to a rim 225 having a diameter that is larger than the main body 215. The interior diameter of the cap 210 at the rim 225 may also be larger than the interior diameter at the main body 215. As shown in FIGS. 3D-E, the interior surface of the rim 225 may include stepped portions that form shoulders that have a shape and configuration generally complementary to the stepped portions 290 of hub 270. As described above, these complementary features may assist in fixing the hub 270 to the cap 210, for example via ultrasonic welding, although other modalities (e.g. adhesives) may be suitable for the fixation.

Referring to FIG. 3D, the cap 210 may include an interior flange 230 extending radially inwardly from the main body 215, about halfway along the length of the main body 215. The interior flange 230 may define a substantially circular aperture 235 at or near a radial center of the cap 210, such that the aperture 235 is substantially coaxial with aperture 280 and catheter 600. With this configuration, a generally cylindrical recess may be formed, the recess having an open proximal end, and being bounded by the main body 215 and, at its distal end, the interior flange 230.

Figure 3F:
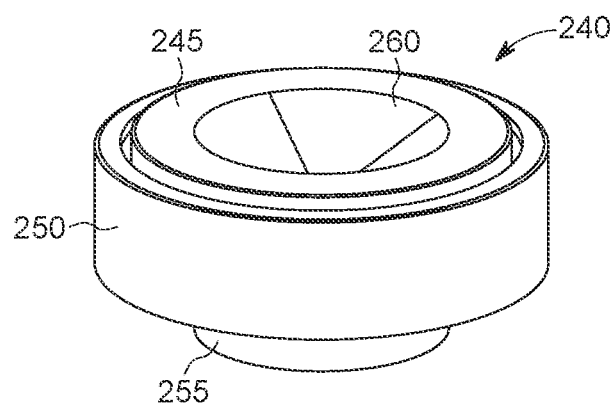
FIG. 3F is a top perspective view of a hemostasis valve of the hemostasis valve assembly of 3A.

Referring now to FIGS. 3B, 3D, and 3F, the hemostasis valve assembly 200 may include a hemostasis valve 240 positioned therein. As best shown in FIG. 3F, the hemostasis valve 240 may include a proximal section 245, a flanged section 250, and a distal section 255. The proximal section 245 may include a generally conical recess extending in a direction toward the distal section 255, the contours of which may assist in guiding a device into and through the hemostasis valve 240. Each of these three valve sections may have a generally circular or cylindrical shape (which may or may not include a taper), with the flanged section 250 having a larger outer diameter than the proximal section 245 and the distal section 255, and the distal section 255 having a smaller outer diameter than the proximal section 245.

Figure 3G:
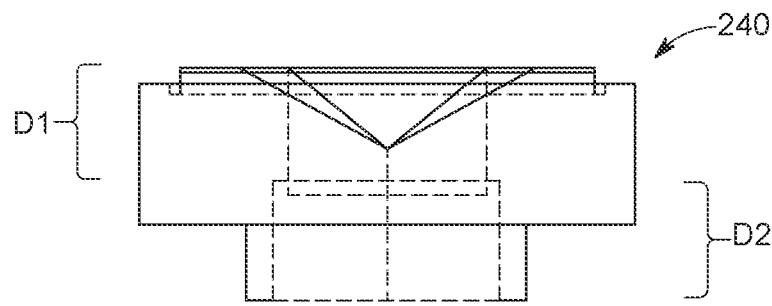
FIGS. 3G-H are side and top views, respectively, of the hemostasis valve of FIG. 3F illustrating slits forming the valve functionality.
Figure 3H:
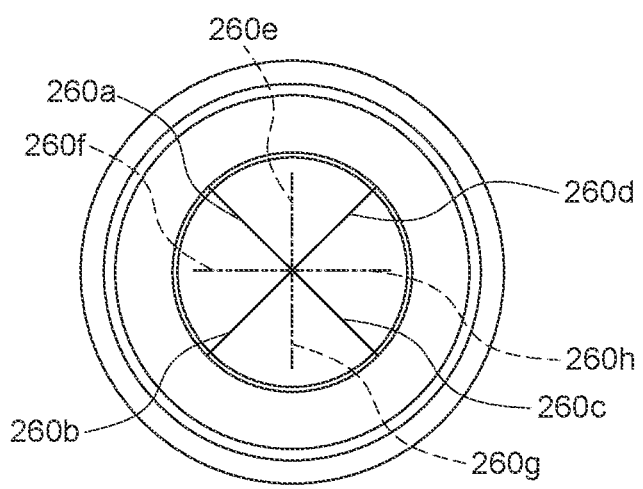

The hemostasis valve 240 is preferably formed as a single integral member, and one or more cuts or slits are formed therein to create the actual valve functionality. One particular way of creating the valve functionality is described directly below, but it should be understood that other methodologies and other resulting valve structures may be suitable for use instead of the particular example shown and described herein. For example, FIGS. 3G-H are side and top views, respectively, of the hemostasis valve 240 with slits made therein illustrated. In this particular example, four slits are formed in the proximal section 245 extending toward the distal section, and four slits are formed in the distal section 255 extending toward the proximal section, each group of four slits being formed in an "X" configuration at a spacing of about 90 degrees between adjacent slits, with the two groups of slits being offset rotationally from each other by about 45 degrees.

In particular, referring to FIGS. 3G-H, four slits 260a-d are formed in the proximal section 240, each slit 260a-d extending a depth D1 toward the distal section 255. Each slit 260a-d is spaced about 90 degrees from an adjacent slit to form the cross or "X"-shape shown. These slits 260a-d may be thought of as forming flaps 260, labeled in FIG. 3F, having generally triangular or wedge shapes. The depth D1 may extend a depth into the flange section 250, but stop short of the distal section 255. The four slits 260a-d intersect at a central intersection point that extends a distance or depth to form a line where the slits intersect. A second group of slits 260e-h are formed in the distal section 255 extending a depth D2 toward the proximal section 245, having substantially the same configuration as slits 260a-d, except being offset, for example by about 45 degrees, relative to slits 260a-d. In particular, as shown in FIG. 3H, the four slits 260e-h form a cross or "X"-shape, with each slit spaced about 90 degrees from an adjacent slit in the group, and the four slits 260e-h meeting at a central intersection point that extends a distance of depth to form a line where the slits intersect. The pathway between the proximal section 245 and the distal section 255 is completed by the two intersection lines of the two groups of slits 260a-d, 260e-h both overlapping for the small distance by which depths D1 and D2 overlap, as shown in FIG. 3G.

When the hemostasis valve assembly 200 is assembled, the outer circumference of the flanged section 250 may be in contact with an inner surface of the main body 215 of the cap 210, just distal to the interior flange 230. The proximal section 245 of the hemostasis valve 240 may be in contact with a distal surface of the interior flange 230, with the center of the hemostasis valve 240, where the flaps 260 converge, substantially coaxial with the circular aperture 235 defined by the interior flange 230, as best shown in FIG. 3D. The distal section 255 of the hemostasis valve 240 may extend into the cylindrical recess 295 of the hub 270. As best shown in FIG. 3D, the distal section 255 may include an outer rim that is substantially coaxial with the central aperture 280 of the hub 270.

When the hemostasis valve assembly 200 is assembled, the connection between cap 210 and hub 270 is fluid-tight such that, in order for any fluid (or other objects) to pass into the cap 210 and through the hub 270 to the catheter 600, the fluid must pass through hemostasis valve 240. In the absence of applied forces, the flaps 260 of the hemostasis valve 240 create a fluid-tight seal so that fluid is prevented from passing through the hemostasis valve 240. It should be understood that hemostasis valves that have other specific configurations than that shown may be suitable for use with the hemostasis valve assembly 200.

Typically, hemostasis valves such as hemostasis valve 240 have a soft durometer, for example from about 20-70 Shore A durometer, and are typically formed of silicone and/or urethane and/or other similar materials. If a hemostasis valve is intended to allow a relatively large device to pass therethrough, the hemostasis valve will typically require a relatively large diameter and/or a relatively large thickness. As hemostasis valves get larger and/or thicker, it may require more force to push a device through the seal, for example because the seal may provide greater resistance against such passage. Also, at least partially because of the low or soft durometer of the material forming a hemostasis valve, one or more drops of silicone oil (or other lubricant) are typically provided by the valve manufacture in the slits to help ensure that the flaps do not stick together, particularly if the valve is sitting on a shelf for a period of time between manufacture and use. The lubricant may be applied directly to the material of the valve or in other embodiments the lubricant may infuse or self-leach into the material. The requirement for a device to have a relatively large column force to easily pass through a hemostasis valve, as well as the possible contamination of that device with pre-applied or infused silicone oil (or another lubricant) as it passes through the valve, may be generally undesirable features, depending on the particular device being passed through the seal. The hemostasis valve assembly 200 described above, in combination with the hemostasis valve knob 300 described below, may overcome one or both of these possible undesirable features.

Figure 4A:
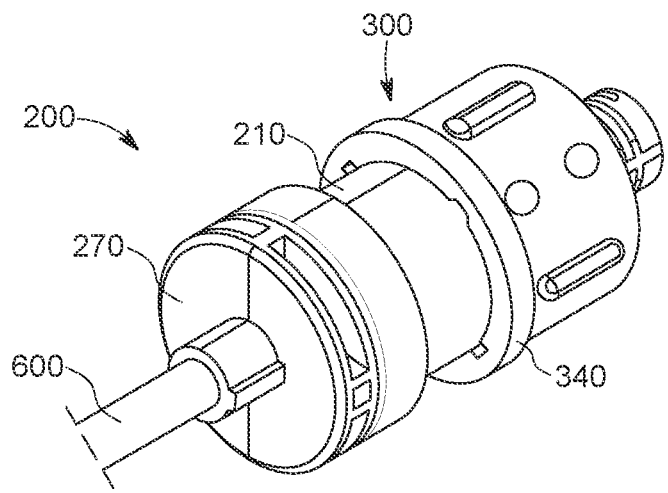
FIG. 4A is perspective view of the hemostasis valve assembly of FIG. 3A assembled to a hemostasis valve knob.
Figure 4B:
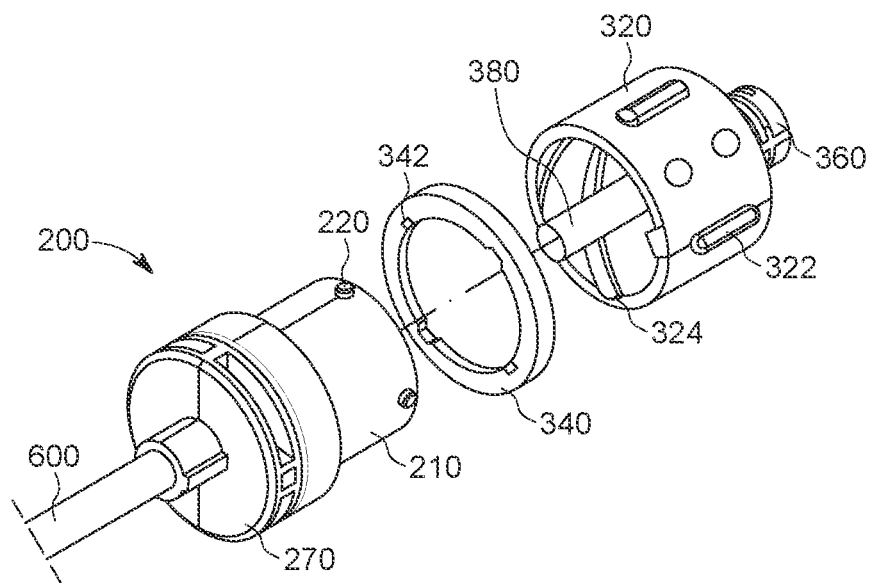
FIG. 4B is an exploded view of the hemostasis valve assembly and the hemostasis valve knob of FIG. 4A.

FIG. 4A shows the hemostasis valve assembly 200 assembled to the hemostasis valve knob 300, with FIG. 4B showing a corresponding exploded view. The hemostasis valve knob 300 may include a main body 320, a retaining ring 340, a bypass hub 360, and a bypass tube 380.

Figure 4C:
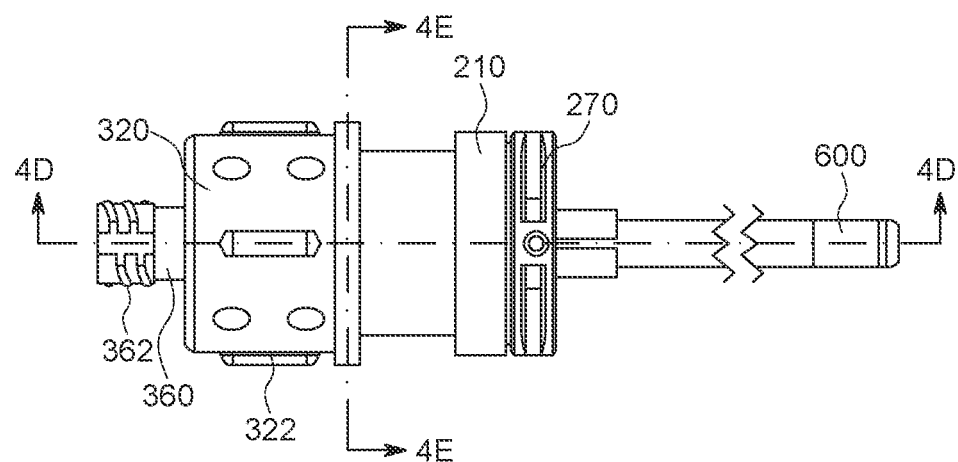
FIG. 4C is a side view of the hemostasis valve assembly and knob of FIG. 4A.
Figure 4D:
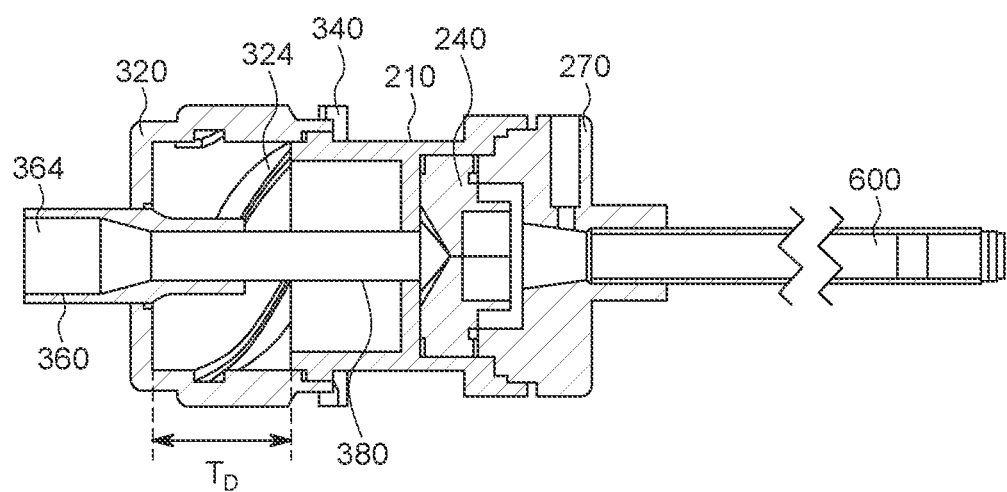
FIG. 4D is a cross-section of the hemostasis valve assembly and knob of FIG. 4A taken along the section line 4D-4D of FIG. 4C.

Referring generally to FIGS. 4A-D, the main body 320 may be generally cylindrical and may include texturization on an outer surface to enhance a user's grip on the main body 320. In the illustrated example, the main body 320 includes four raised knurls 322 at equal circumferential spacing to assist a user in torqueing the main body 320. However, it should be understood that other numbers, types, and spacing of texturization features may be provided instead of the raised knurls 322. The main body 320 may have a substantially open distal end, and an inner diameter that is sized to fit over the outer diameter of the main body 215 of cap 210. As best shown in FIGS. 4B and 4D, the inner surface of main body 320 may include a plurality of curved channels or recesses 324, for example each in a generally helical configuration. Each curved recess 324 may extend to the terminal distal end of the main body 320, and may have a width and a depth sized to receive a corresponding protrusion 220 therein. With this configuration, when the main body 320 is assembled over the main body 215, and each protrusion 220 is received within a corresponding curved recess 324, rotating the main body 320 will translate the hemostasis valve knob 300 toward or away from the hub 270 of the hemostasis valve assembly 200, as described in greater detail below. For example, as shown in FIG. 4D, rotation of the main body 320 allows for distal translation or advancement of the main body 320 (along with the bypass hub 360 and bypass tube 380) a maximum available travel distance $T_D$, until the interior proximal face of the main body 320 contacts that proximal end of the cap 210. The actual available travel distance may be smaller, depending on the axial length of the recesses 324, for example. Although four curved recesses 324 are shown, more or fewer may be provided, preferably with equal number and spacing as the protrusions 220. And although referred to as a knob that is rotatable, the hemostasis valve knob 300 may also be referred to as an actuator that activates by rotation or other non-rotational movements.

Figure 4E:
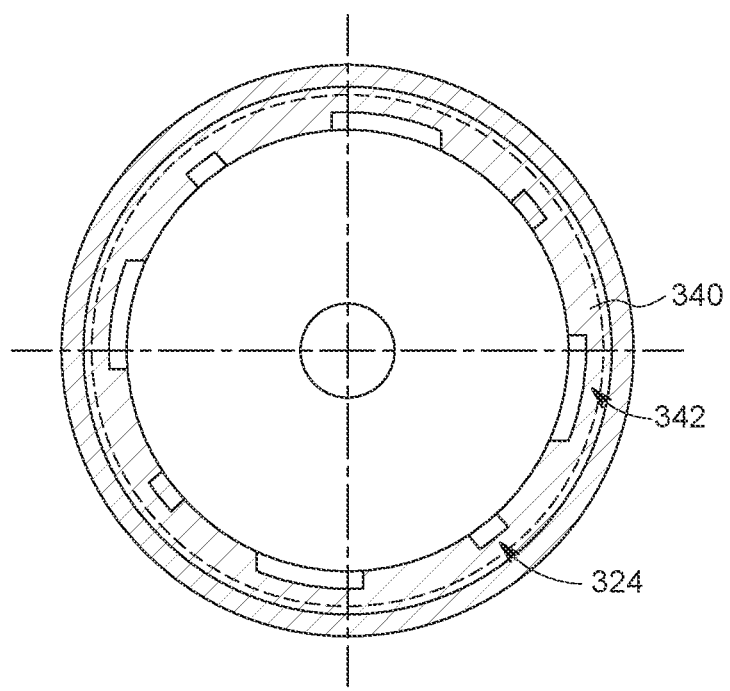
FIG. 4E is a cross-section of the hemostasis valve assembly and knob of FIG. 4A taken along the section line 4E-4E of FIG. 4C, with certain components omitted from the view.

Retaining ring 340 may be a generally annular member that is sized to mate with the terminal distal surface of the main body 320. In particular, the retaining ring 340 may have a distal face with an inner diameter that is slightly smaller than the outer diameter of the main body 320, and an outer side wall that has an inner diameter that is about equal to or slightly larger than the outer diameter of the main body 320. As shown in FIG. 4D, this size configuration allows the retaining ring 340 to snap over the terminal distal end of the main body 320. As best illustrated in FIGS. 4A-B, the retaining ring 340 may include a plurality of recesses 342 in the distal face thereof, preferably in the same number and relative spacing as protrusions 220 and curved recesses 340. The recesses 342 are sized and spaced so that, when each recess aligns with a corresponding protrusion 220, the retaining ring 340 may slide axially over the main body 215 of cap 210. However, if the recesses 342 are not aligned with corresponding protrusions 220, there is not enough clearance for the retaining ring 340 to slide axially past the protrusions 220. This configuration may help with assembling the main body 320 to the main body 215, with the retaining ring 340 ensuring that the main body 320 cannot disconnect from the main body 215. For example, during assembly, the retaining ring 340 may be oriented with recesses 342 aligned with protrusions 220 and slid distally over the main body 215. Then, the retaining ring 340 may be rotated, for example about 45 degrees, so that the recesses 342 no longer align with the protrusions 220. Then, the main body 320 may be coupled to the main body 215 with the protrusions 220 received within curved channels 324. The main body 320 may then be fixed to the retaining ring 340, such that the terminal distal ends of the curved recesses 324 are out of alignment with the recesses 342 of the retaining ring 340. The method for fixing may be any suitable method, including adhesives, ultrasonic welding, etc. With this configuration, the retaining ring 340 prevents the main body 320 from slipping off the main body 215 as it moves proximally away from the main body 215 upon rotation. FIG. 4E illustrates the coupling of the retaining ring 340 to the main body 320, with other components omitted for clarity. As can be seen, the recesses 342 of the retaining ring 340 are out of alignment with the ends of the curved recesses 324 in the main body 320.

Referring to FIGS. 4C-D, the hemostasis valve knob 300 includes a bypass hub 360 and a bypass tube 380 extending through a proximal surface of the main body 320. The bypass hub 360 may have a generally cylindrical outer surface, and may include threads 362 or another mechanism to facilitate coupling to other devices used in conjunction with delivery device 10. The bypass hub 360 may be formed integrally with, or formed separately and then coupled to, the main body 320. The bypass hub 360 may define a lumen 364 therethrough, and the lumen 364 may be tapered in the distal direction. The lumen 364 is preferably coaxial with the other lumens and openings within the hemostasis valve assembly 200 such as aperture 235, aperture 280, the overlapping openings of hemostasis valve 240, and is also preferably coaxial with the catheter 600.

Referring now to FIG. 4D, the bypass tube 380 extends distally from the bypass hub 360. The bypass tube 380 is preferably generally cylindrical with an outer diameter that is about equal to or just smaller than the interior diameter of aperture 235. The bypass tube 380 may be formed integrally with the bypass hub 360, for example via injection molding, in which case suitable materials may include acrylonitrile butadiene styrene ("ABS"). In other embodiments, the bypass tube 380 may be formed of materials such as polyoxymethylene (e.g. under the tradename Delrin), etched polytetrafluoroethylene, polyether block amide (e.g. under the tradename Pebax), or other suitable materials such as Nylon (e.g. lined Nylon 12 tubing). The bypass tube 380 preferably has a relatively high column strength, such that it may easily pass through hemostasis valve 240 without buckling or otherwise being damaged as it translates distally. For example, the bypass tube 380 may have a column strength that is greater than the column strength of the medical device that is to be passed through the bypass tube. The bypass tube 380 preferably has a length so that, when the main body 320 is in its proximalmost position relative to the cap 210, the distalmost end of the bypass tube 380 is positioned within aperture 235 just proximal of the hemostasis valve 240.

Figure 4F:
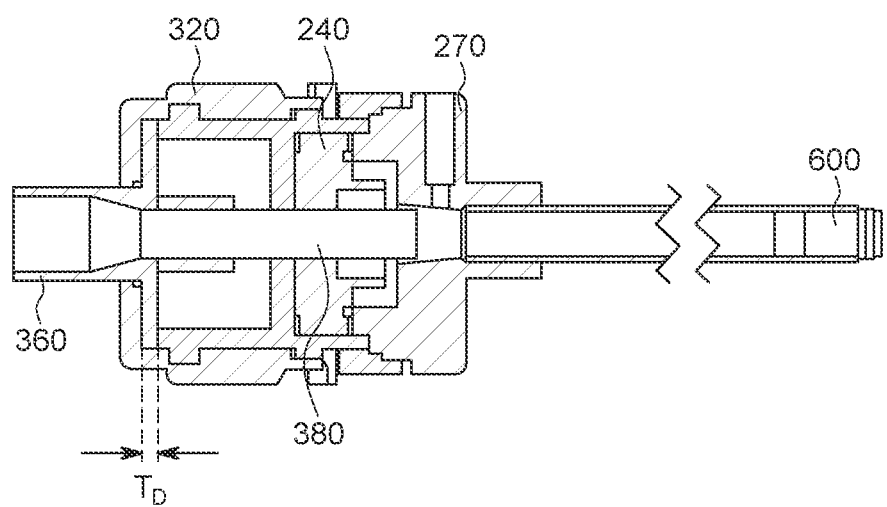
FIG. 4F is a cross-section of the hemostasis valve assembly and knob of FIG. 4A taken along the section line 4D-4D of Fic. 4C after activation of the valve bypass feature.

It should be understood that the hemostasis valve assembly 200 and knob 300 are illustrated in FIGS. 4A, 4C, and 4D in a sealed or first condition, in which the main body 320 is in its proximalmost position relative to the cap 210. In this condition, as noted above, the distalmost end of the bypass tube 380 is positioned just proximal to the hemostasis valve 240, so that the bypass tube 380 does not traverse the hemostasis valve 240. A user may transition the hemostasis valve assembly 200 and knob 300 into an open or second condition by rotating the main body 320 relative to the cap 210, forcing the hemostasis valve knob 300 to translate distally until the bypass tube 380 passes through the hemostasis valve 240. This open or second condition is illustrated in FIG. 4F. As shown in FIG. 4F, the main body 320 of the hemostasis valve knob 300 has been rotated to advance the main body 320, as well as the retaining ring 340, bypass hub 360, and bypass tube 380 distally relative to the hemostasis valve assembly 200. The completion of the advancement can be seen by, for example, comparing the available travel distance $T_D$ shown in FIG. 4D having been decreased to substantially zero, with the inner face of the proximal main body 320 abutting the proximal end of cap 210. In this second or open condition, the bypass tube 380 fully traverses the hemostasis valve 240, with the distal terminal end of the bypass tube 380 positioned within or adjacent to central aperture 280. Thus, in the first or sealed condition shown in FIG. 4D, the hemostasis valve 240 is closed and the lumens or openings distal to the hemostasis valve 240 are sealed from the lumens or openings proximal to the hemostasis valve 240. However, in the second or open condition shown in FIG. 4F, the bypass tube 380 forces the hemostasis valve 240 to remain open, putting the lumens or openings distal of the hemostasis valve 240 in fluid communication with the lumens or openings proximal to the hemostasis valve 240.

Figure 5A:
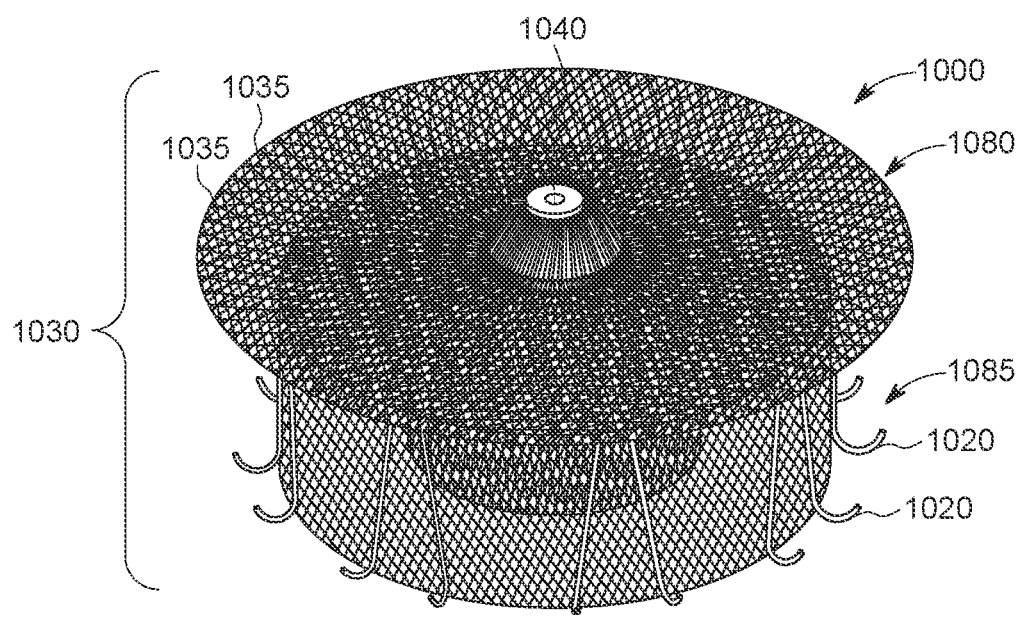
FIG. 5A is a perspective view of an occluder in an expanded or deployed condition.

FIG. 5A is a perspective view of an occluder 1000, which may be a LAA occluder. Very generally, occluder 1000 includes an occluding material forming a tubular structure 1030, the occluding material being a braided metal fabric, which may be formed by braiding a plurality of strands 1035, which may be strands of nickel titanium alloy (e.g. under the tradename Nitinol), together and shape set (e.g. via heat setting) to the shape shown in FIG. 5A. When in the shape-set or expanded condition (e.g. in the absence of applied forces), the occluder 1000 may include a generally disk-shaped portion 1080 configured to abut an ostium of the patient's LAA, and a second generally cylindrical portion 1085 configured to be received within the patient's LAA. In some embodiments, the disk-shaped portion 1080 may be coupled to the cylindrical portion 1085 via a small diameter transition portion. The cylindrical portion 1085 may include one or more hooks 1020 configured to engage tissue within the LAA upon deployment. The disk-shaped portion 1080 may include a connector 1040, which may for example include internal threads, for coupling to a delivery cable 1300.

Figure 5B:
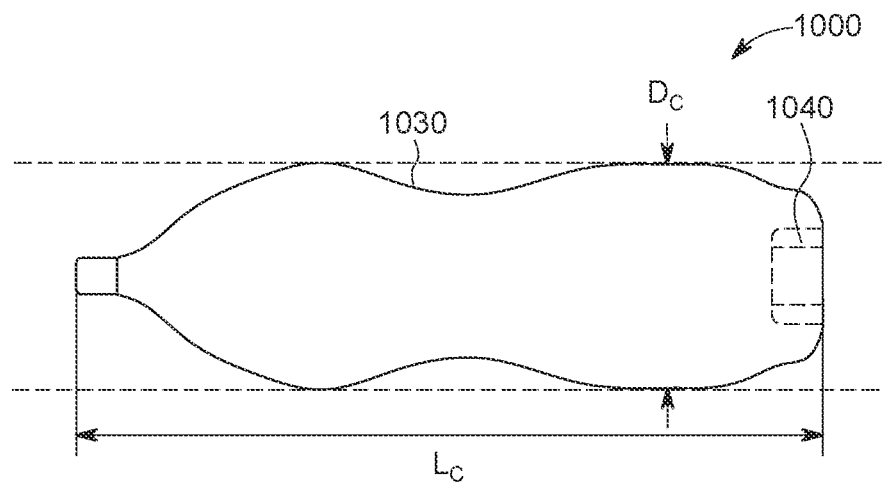
FIG. 5B is a schematic view of the occluder of FIG. 5A in a collapsed or delivery condition.
Figure 5C:
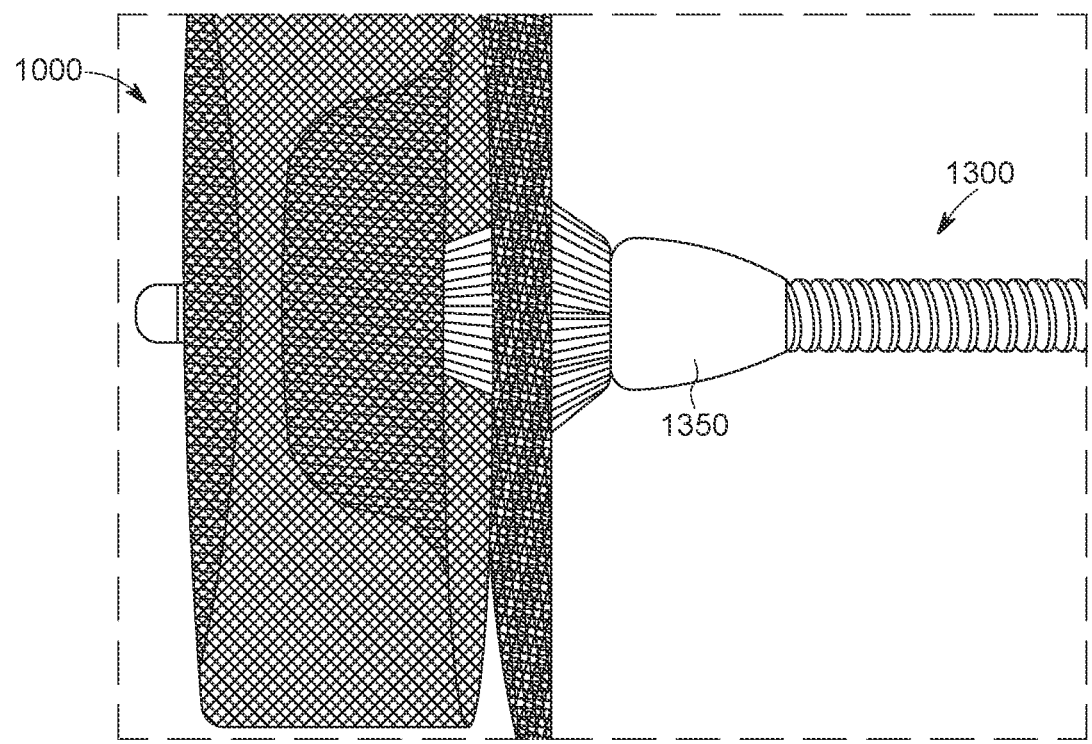
FIG. 5C is a side view of the occluder of FIG. 5A coupled to a delivery cable.

FIG. 5B illustrates occluder 1000 in a collapsed condition, having a collapsed diameter Dc smaller than the diameter of the disk-shaped portion 1080 and the cylindrical portion 1085 when in the expanded condition shown in FIG. 5A, and a collapsed length Lc longer than the length of the occluder in the expanded condition shown in FIG. 5A. FIG. 5C illustrates the delivery cable 1300 coupled to the connector 1040, for example via a threaded hub 1350 of the delivery cable 1300 that has been threaded into the connector 1040.

An exemplary use of the delivery device 10 with the integrated hemostasis bypass valve for delivering occluder 1000 is described below. At the beginning of the procedure (or in preparation thereof), the delivery device 10, including dilator 700, may be removed from sterile packaging. The user preferably confirms that the hemostasis valve knob 300 is in the first, sealed position such that the hemostasis valve 200 is closed. If the hemostasis valve knob needs to be adjusted, the user may rotate the hemostasis valve knob 300, for example by turning it counter-clockwise relative to the hemostasis valve assembly 200, to retract the bypass tube 380 so that it does not pass through the hemostasis valve 240. The catheter 600 and the dilator 700 may be wiped with sterile gauze dampened with sterile saline to remove any foreign material that may be on the components. The user may then pass the dilator 700 through the delivery device 10 until the distal end of the dilator 700 passes the distal end of the catheter 600. Even though the hemostasis valve knob 300 is in the first, sealed position, the dilator 700 has enough column strength to readily pass through the hemostasis valve 240 without assistance of the bypass tube 380, without any buckling or damage occurring to the dilator 700. When the dilator 700 is fully inserted through the delivery device 10, the connector 710 (or a threaded collar associated with the connector 710) may be rotated to couple to the bypass hub 360, for example by inner threads of the connector 710 engaging outer threads 362 of the bypass hub. The dilator 700 is now coupled to the remaining portions of the delivery device 10 as a single unit. Access may be gained to the patient via any suitable method, and a guidewire may be advanced into the patient's vasculature until it reaches the patient's left atrium, LAA, or pulmonary vein. Prior to or during introduction of the guidewire, a puncture may be made through the patient's atrial septum if the delivery route is, for example, through the patient's femoral vein and to the right atrium via the inferior vena cava, with the septal puncture allowing the guidewire and other components to traverse the atrial septum into the left atrium. With the guidewire in place, the dilator 700 (and the remainder of the delivery device 10 to which it is coupled) may be advanced over the guidewire into the patient until the distal end of the delivery device 10 reaches the left atrium or LAA. With the distal end of the delivery device 10 in the desired location, the connector 710 may be rotated to decouple it from the bypass hub 360, and the dilator 700 may be withdrawn from the catheter 600, preferably slowly to prevent any ingress of air. After the dilator 700 is fully removed, the guidewire may next be fully removed from the delivery device 10 and the patient, although the guidewire may instead be simultaneously removed with the dilator 700.

Figure 5D:
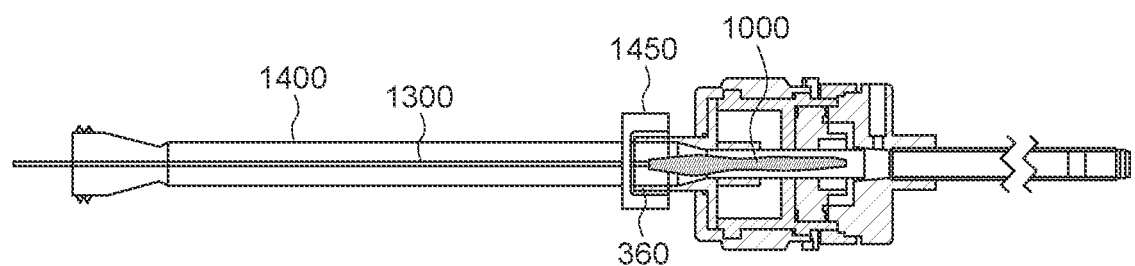
FIG. 5D is a highly schematic view of the occluder of FIG. 5A being passed through a loading tube coupled to the hemostasis valve knob and hemostasis valve assembly of FIG. 4F.

With the distal end of the catheter 600 in the desired position, the occluder 1000 may be introduced into and through the delivery device 10. As shown in FIG. 5D, a loading tube 1400 provided with the occluder 1000 may be coupled to the bypass hub 360, for example by rotating a threaded connector 1450 (or a threaded collar associated therewith) onto the bypass hub 360. The occluder 1000 may be pushed through the loading tube 1400 toward the hemostasis valve assembly 200 while the occluder 1000 is in the collapsed condition, by pushing delivery cable 1300. Prior to the occluder 1000 reaching the hemostasis valve 240, the user rotates the hemostasis valve knob 300, for example in clockwise direction, so that the bypass tube 380 advances into and through the hemostasis valve 240. However, in some embodiments, it may be appropriate to activate the bypass mechanism to get a wet-to-wet connection with the loading tube 1400 prior to the occluder 1000 reaching the hemostasis valve 240. Either way, with the hemostasis valve knob 300 in the second, open condition, the user may push the cable 1300 to advance the collapsed occluder through the bypass tube 380, bypassing the need for the occluder 1000 to contact the hemostasis valve 240 directly as the occluder 1000 passes through the hemostasis valve assembly 200. At any point after the occluder 1000 has advanced distally beyond the hemostasis valve 240, and prior to the occluder 1000 being deployed from the catheter 600, the hemostasis valve knob 300 may again be rotated to revert the hemostasis valve knob 300 into the first, closed condition. The cable 1300 preferably is able to readily pass through the closed hemostasis valve 240 without the assistance of the bypass tube 380. The user may continue pushing the delivery cable 1300 until the occluder reaches the distal end of the catheter 600, and then deploy the occluder 1000 from the distal end of the catheter 600, allowing the occluder 1000 to self-expand into the LAA to occluder the LAA. This process may be coupled with steering of the catheter 600 using the handle 100 and deflection knob 500, if steering capabilities are included in the delivery device 10. With the occluder 1000 deployed in the desired position, the cable 1300 may be decoupled from the occluder 1000, for example via rotation of the cable 1300, and the cable 1300 may be withdrawn from the delivery device 10.

As described above, there are at least two benefits that may be provided by the hemostasis valve bypass components. First, various medical devices that are collapsible for delivery through a catheter may have low column strength, especially compared to components like dilator 700. Occluder 1000 is formed of a braided mesh of strands of nickel titanium alloy, which may result in the occluder 1000 having a low column strength. Without the bypass tube 280, as the user pushed the occluder 1000 through the hemostasis valve 240, the occluder 1000 might buckle and become damaged as it encounters resistance from the hemostasis valve 240. Further, if the hemostasis valve 240 has silicone oil or another lubricant from when it was manufactured, that silicone oil may transfer to the occluder 1000, effectively contaminating the occluder with that substance. The bypass tube 280 solves both of these problems, by eliminating resistance that the occluder 1000 would encounter from the hemostasis valve 240, as well as ensuring no transfer of contaminants occurs since there is no direct contact between the occluder 1000 and the hemostasis valve 240. Further, the embodiments disclosed herein allow for the hemostasis valve assembly 200 and hemostasis valve knob 300 to be integrated with the remainder of the delivery device 10. In other words, the functionality of the bypass tube 380 is provided without the need for another separate device beyond the delivery device 10, increasing the convenience and decreasing the procedure time that would be required by having the bypass tube 380 a fully separate component.

Although the integrated hemostasis bypass valve described herein may be particularly useful for the LAA occluder 1000 device described herein, it should be understood that this particular use is merely exemplary. For example, the integrated hemostasis bypass valve described herein may be particularly useful for other occluders formed of braided metal, including septal occluders, patent ductus arteriosus ("PDA") occluder devices, patent foramen ovale ("PFO") closure devices, etc. It should further be understood that the integrated hemostasis bypass valve described herein may work well with other occluders, including those not formed from a braided mesh, or any other medical device, whether an occluder or not and whether formed of braided mesh or not, if that medical device has relatively low column strength and/or if it would be undesirable for that medical device to be contaminated with silicone oil or another lubricant from direct contact with a hemostasis valve.

According to one aspect of the disclosure, a delivery device comprises:
    a handle;
    a catheter sheath extending distally from the handle;
    a hemostasis valve positioned within the handle, the hemostasis valve being located proximal the catheter sheath and distal to a proximal end of the handle; and
    a hemostasis bypass assembly coupled to the handle, the hemostasis bypass assembly including a bypass tube coupled to an actuator, the actuator configured to be transitioned between a first condition in which a distal end of the bypass tube is positioned proximal to the hemostasis valve and the hemostasis valve is closed, and a second condition in which the distal end of the bypass tube traverses the hemostasis valve and the hemostasis valve is opened; and/or
  the hemostasis bypass assembly is integrated with the handle; and/or
  the hemostasis bypass assembly is coupled to the proximal end of the handle; and/or
  the hemostasis valve is formed of urethane or silicone; and/or
  the hemostasis valve is part of a hemostasis valve assembly, the hemostasis valve assembly including a main body extending proximal of the hemostasis valve and a hub extending distally of the hemostasis valve, the main body and the hub maintaining the hemostasis valve therebeween; and/or
  the actuator is a rotatable knob; and/or
  the main body includes one or more protrusions extending radially outwardly from the main body, and the rotatable knob includes one or more curved recesses on an interior surface thereof, the one or more protrusions received within a corresponding one or more curved recesses on the interior surface of the rotatable knob, such that rotation of the rotatable knob translates bypass tube toward or away from the hemostasis valve; and/or
  the hemostasis bypass assembly includes a retaining ring that overlies the main body of the hemostasis valve assembly, a proximal end of the retaining ring being coupled to a distal end of the rotatable knob; and/or
  the main body of the hemostasis valve assembly includes an interior flange defining a central aperture, and when the actuator is in the first condition, the a distal end of the bypass tube is received within the central aperture; and/or the bypass tube is coaxial with the central aperture, the hemostasis valve, and the catheter sheath; and/or a bypass hub at the proximal end of the actuator, the bypass hub coupled to the bypass tube, the bypass hub and the bypass tube including a continuous lumen extending therethrough; and/or the bypass hub includes external threading; and/or the hemostasis valve includes a proximal section and a distal section, a first group of four slits formed in the proximal section and extending a first depth toward the distal section, and a second group of four slits formed in the distal section and extending a second depth toward the proximal section; and/or the first group of four slits are formed at about 90 degrees relative to each other in a first "X"-configuration, and the second group of four slits are formed at about 90 degrees relative to each other in a second "X"-configuration, the first "X"-configuration being offset by about 45 degrees relative to the second "X"-configuration; and/or the first depth overlaps with the second depth to form a pathway from the first group of four slits to the second group of four slits; and/or a deflection knob coupled to the handle, the deflection knob being rotatable about a longitudinal axis of the handle to activate one or more pull wires coupled to a distal tip of the catheter sheath to deflect the distal tip of the catheter sheath.

According to another embodiment of the disclosure, a medical device system comprises:

the delivery device described in the paragraph above; and a collapsible and expandable medical device, the medical device configured to be received within the delivery device in a collapsed condition and configured to pass through the delivery device while in the collapsed condition, the medical device having a first column strength in the collapsed condition that is less than a column strength of the bypass tube; and/or the medical device is a left atrial appendage occlusion ("LAAO") device; and/or the LAAO device is formed of a braided mesh of metal strands; and/or the metal strands are formed of a nickel titanium alloy.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A delivery device for a collapsible and expandable medical device, the delivery device comprising:

a handle;

a catheter sheath extending distally from the handle;

a hemostasis valve positioned within the handle, the hemostasis valve being located proximal the catheter sheath and distal to a proximal end of the handle; and a hemostasis bypass assembly coupled to the handle, the hemostasis bypass assembly including a bypass tube coupled to an actuator, the actuator configured to be transitioned between a first condition in which a distal end of the bypass tube is positioned proximal to the hemostasis valve and the hemostasis valve is closed, and a second condition in which the distal end of the bypass tube traverses the hemostasis valve and the hemostasis valve is opened, wherein the hemostasis valve is part of a hemostasis valve assembly, the hemostasis valve assembly including a main body extending proximal of the hemostasis valve and a hub extending distally of the hemostasis valve, the main body and the hub maintaining the hemostasis valve therebetween, wherein the actuator is a rotatable knob, wherein the main body includes one or more protrusions extending radially outwardly from the main body, and the rotatable knob includes one or more curved recesses on an interior surface thereof, the one or more protrusions received within a corresponding one or more curved recesses on the interior surface of the rotatable knob, such that rotation of the rotatable knob translates the bypass tube toward or away from the hemostasis valve, wherein the hemostasis bypass assembly includes a retaining ring that overlies the main body of the hemostasis valve assembly, a proximal end of the retaining ring being coupled to a distal end of the rotatable knob, wherein in an assembled condition of the delivery device, the retaining ring is fixed to the rotatable knob wherein the retaining ring includes one or more recesses being sized and spaced to align with the one or more protrusions.

2. The delivery device of claim 1, wherein the hemostasis bypass assembly is integrated with the handle.

3. The delivery device of claim 2, wherein the hemostasis bypass assembly is coupled to the proximal end of the handle.

4. The delivery device of claim 1, wherein the hemostasis valve is formed of urethane or silicone.

5. The delivery device of claim 1, wherein the main body of the hemostasis valve assembly includes an interior flange defining a central aperture, and when the actuator is in the first condition, the distal end of the bypass tube is received within the central aperture.

6. The delivery device of claim 5, wherein the bypass tube is coaxial with the central aperture, the hemostasis valve, and the catheter sheath.

7. The delivery device of claim 1, further comprising a bypass hub at the proximal end of the actuator, the bypass hub coupled to the bypass tube, the bypass hub and the bypass tube including a continuous lumen extending therethrough.

8. The delivery device of claim 7, wherein the bypass hub includes external threading.

9. The delivery device of claim 1, wherein the hemostasis valve includes a proximal section and a distal section, a first group of four slits formed in the proximal section and extending a first depth toward the distal section, and a second group of four slits formed in the distal section and extending a second depth toward the proximal section.

10. The delivery device of claim 9, wherein the first group of four slits are formed at about 90 degrees relative to each other in a first "X"-configuration, and the second group of four slits are formed at about 90 degrees relative to each other in a second "X"-configuration, the first "X"-configuration being offset by about 45 degrees relative to the second "X"-configuration.

11. The delivery device of claim 10, wherein the first depth overlaps with the second depth to form a pathway from the first group of four slits to the second group of four slits.

12. The delivery device of claim 1, further comprising a deflection knob coupled to the handle, the deflection knob being rotatable about a longitudinal axis of the handle to activate one or more pull wires coupled to a distal tip of the catheter sheath to deflect the distal tip of the catheter sheath.

13. The delivery device of claim 1, wherein in a pre-assembled condition of the delivery device, the retaining ring is configured to slide over the main body while the one or more recesses are aligned with the one or more protrusions, and in the assembled condition of the delivery device, the one or more recesses are not aligned with the one or more protrusions to prevent the retaining ring from sliding off the main body.

14. The delivery device of claim 1, wherein in the assembled condition of the delivery device, the retaining ring is fixed to the rotatable knob by adhesives or ultrasonic welding.

15. A medical device system, comprising:
the delivery device of claim 1; and
the collapsible and expandable medical device, the medical device configured to be received within the delivery device in a collapsed condition and configured to pass through the delivery device while in the collapsed condition, the medical device having a first column strength in the collapsed condition that is less than a column strength of the bypass tube.

16. The medical device system of claim 15, wherein the medical device is a left atrial appendage occlusion ("LAAO") device.

17. The medical device system of claim 16, wherein the LAAO device is formed of a braided mesh of metal strands.

18. The medical device system of claim 17, wherein the metal strands are formed of a nickel titanium alloy.

* * * * *